(12) United States Patent
Strobl et al.

(10) Patent No.: US 8,562,563 B2
(45) Date of Patent: Oct. 22, 2013

(54) POWER INJECTOR SYRINGE CLAMP ASSEMBLY WITH RFID ANTENNA

(75) Inventors: Geoffrey S. Strobl, Williamsburg, OH (US); Chad M. Gibson, Westerville, OH (US); John K. Bruce, Burlington, KY (US)

(73) Assignee: Mallinckrodt LLC, Hazelwood, MO (US)

( * ) Notice: Subject to any disclaimer, the term of this patent is extended or adjusted under 35 U.S.C. 154(b) by 371 days.

(21) Appl. No.: 13/056,177

(22) PCT Filed: Aug. 17, 2009

(86) PCT No.: PCT/US2009/053968
§ 371 (c)(1),
(2), (4) Date: Jan. 27, 2011

(87) PCT Pub. No.: WO2010/021952
PCT Pub. Date: Feb. 25, 2010

(65) Prior Publication Data
US 2011/0130720 A1    Jun. 2, 2011

Related U.S. Application Data

(60) Provisional application No. 61/090,008, filed on Aug. 19, 2008.

(51) Int. Cl.
*A61M 37/00* (2006.01)

(52) U.S. Cl.
USPC ............................................................ 604/131

(58) Field of Classification Search
USPC ............................................................ 604/131
See application file for complete search history.

(56) References Cited

U.S. PATENT DOCUMENTS

| | | | |
|---|---|---|---|
| 7,686,789 B2 * | 3/2010 | Nemoto et al. | 604/246 |
| 8,211,057 B2 * | 7/2012 | Nemoto et al. | 604/121 |
| 2007/0198297 A1 | 8/2007 | Perkins et al. | |
| 2008/0125713 A1 | 5/2008 | Nemoto et al. | |
| 2008/0132839 A1 | 6/2008 | Strobl | |
| 2009/0131756 A1 * | 5/2009 | Nemoto | 600/300 |
| 2009/0156931 A1 * | 6/2009 | Nemoto et al. | 600/432 |
| 2011/0130720 A1 * | 6/2011 | Strobl et al. | 604/131 |
| 2011/0137162 A1 * | 6/2011 | Bruce et al. | 600/432 |
| 2011/0144486 A1 * | 6/2011 | Bruce et al. | 600/432 |

* cited by examiner

*Primary Examiner* — Manuel Mendez
*Assistant Examiner* — Diva K Chander

(57) ABSTRACT

A power injector syringe clamp assembly (300) is disclosed. This clamp assembly (300) includes a first clamp member (302) and a second clamp member (312), where at least one of these clamp members (302, 312) is movable to provide open and closed configurations for the clamp assembly (300). The clamp assembly (300) also includes at least one RFID reader antenna for communicating with at least one RFID tag (336) on a power injector syringe (330), at least when positioned within the clamp assembly (300).

45 Claims, 9 Drawing Sheets

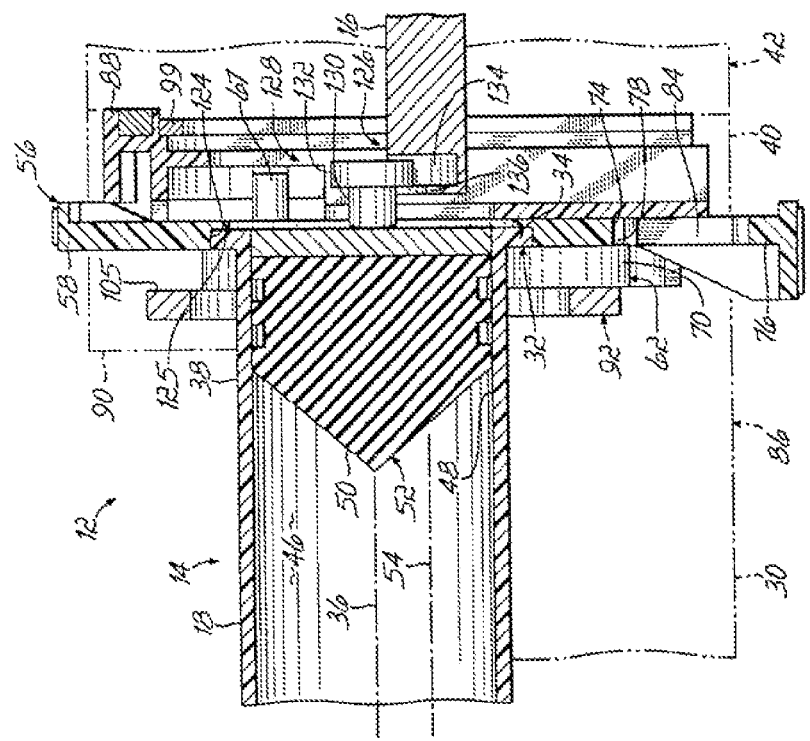
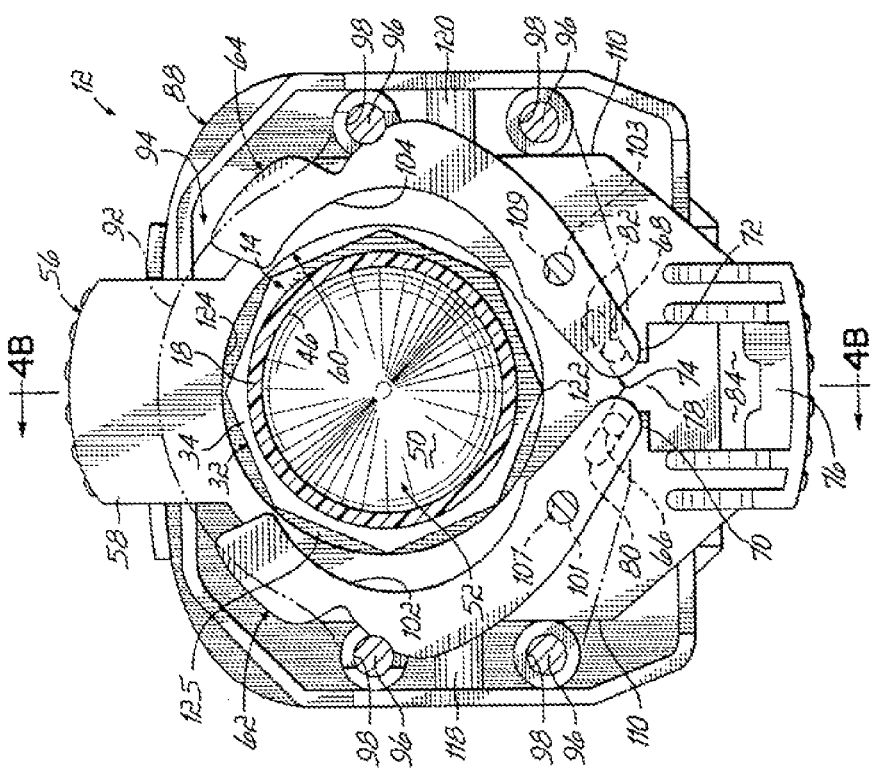
FIG. 4A
FIG. 4B

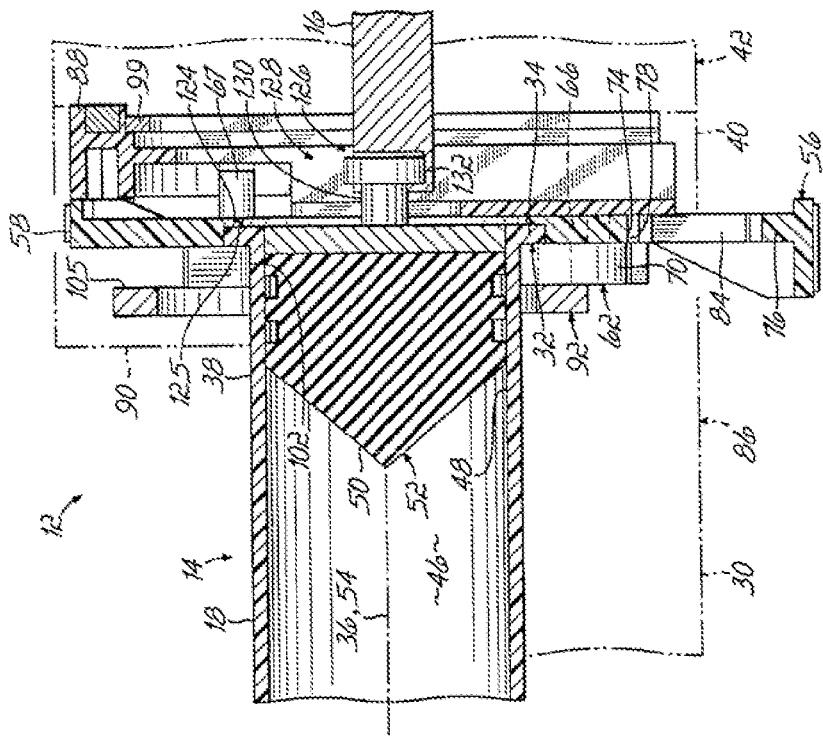
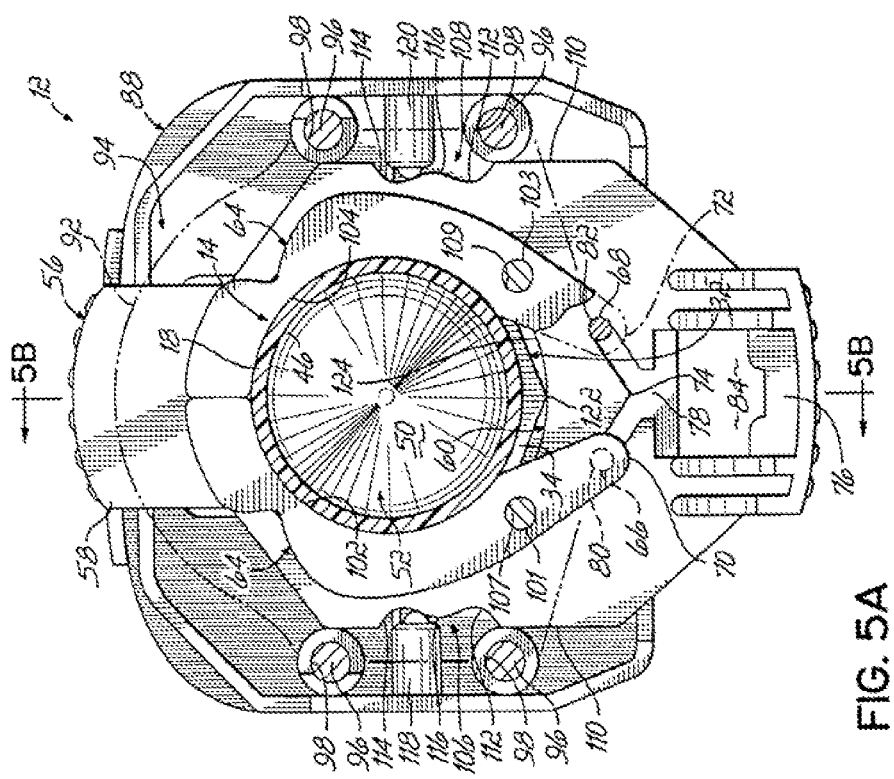
FIG. 5B
FIG. 5A

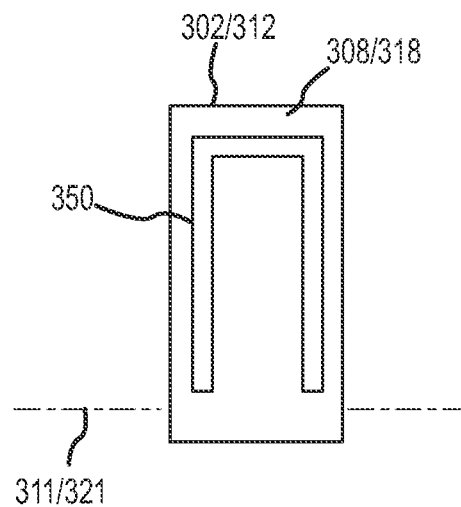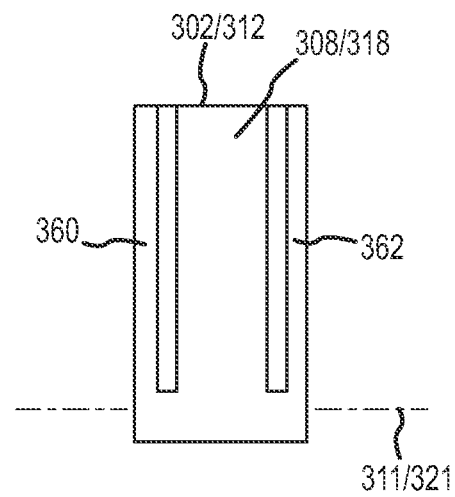
FIG.8A  FIG.8B
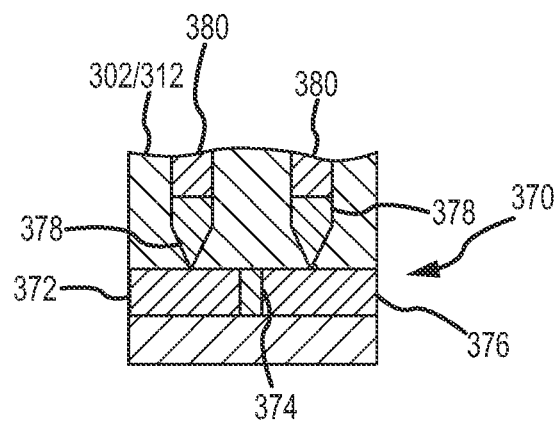
FIG.9

POWER INJECTOR SYRINGE CLAMP ASSEMBLY WITH RFID ANTENNA

RELATED APPLICATIONS

This application is a U.S. National Stage of PCT/US2009/053968, filed 17 Aug. 2009, which claims priority to and is a non-provisional application of U.S. Provisional Patent Application No. 61/090,008 filed on 19 Aug. 2008 entitled "POWER INJECTOR SYRINGE CLAMP ASSEMBLY WITH RFID ANTENNA READER".

FIELD OF THE INVENTION

The present invention generally relates to the field of power injectors and, more particularly, to providing a communication link between a powerhead and syringe for a power injector.

BACKGROUND

Various medical procedures require that one or more medical fluids be injected into the patient. Medical imaging procedures oftentimes involve the injection of a contrast media into the patient, possibly along with saline or other fluids. Other medical procedures involve injecting one or more fluids into a patient for therapeutic purposes. Power injectors may be used for these types of applications.

A power injector generally includes what is commonly referred to as a powerhead. One or more syringes may be mounted to the powerhead in various manners (e.g., detachably; rear-loading; front-loading; side-loading). Each syringe typically includes what may be characterized as a syringe plunger, piston, or the like. Each such syringe plunger is designed to interact with (e.g., contact and/or temporarily interconnect with) an appropriate syringe driver that is incorporated into the powerhead, such that operation of the syringe driver axially advances the associated syringe plunger inside and relative to a barrel of the syringe. One typical syringe driver is in the form of a ram that is mounted on a threaded lead or drive screw. Rotation of the drive screw in one rotational direction advances the associated ram in one axial direction, while rotation of the drive screw in the opposite rotational direction advances the associated ram in the opposite axial direction.

RFID tags are becoming more and more popular in various applications. RFID tags have been addressed in relation to medical applications, and including in relation to power injectors. For instance, it has at least been suggested to dispose an RFID tag on a power injector syringe and encode at least certain information onto such an RFID tag. An RFID reader antenna on or associated with the power injector may be used to read the information from this syringe-mounted RFID tag.

SUMMARY

A first aspect of the present invention is embodied by a power injector syringe clamp assembly (hereafter a "clamp assembly"). The clamp assembly includes a first clamp member having a first RFID reader antenna. The first clamp member is movable to at least assist in defining open and closed configurations for the clamp assembly. Moving the first clamp member into one position may be associated with an open configuration for the clamp assembly (e.g., to allow a power injector syringe to be installed into or removed from the clamp assembly). Moving the first clamp member into another position may be associated with a closed configuration for the clamp assembly (e.g., where the clamp assembly engages and/or is disposed in closely-spaced relation to an installed power injector syringe; where the clamp assembly restrains an installed power injector syringe in at least some manner).

Various refinements exist of the features noted in relation to the first aspect of the present invention. Further features may also be incorporated in the first aspect of the present invention as well. These refinements and additional features may exist individually or in any combination. The first clamp member may be moved in any appropriate manner, including between first and second positions (e.g., for open and closed configurations, respectively, for the power injector syringe clamp assembly). In one embodiment, the first clamp member may utilize a pivotal motion. For instance, the first clamp member may be mounted on a first pivot pin. Power to the first RFID reader antenna may be provided through this first pivot pin.

The above-noted first pivot pin may be formed from an electrically conductive material or combination of materials, and may be electrically interconnected with the first RFID reader antenna in any appropriate manner. For instance, one or more electrical traces, wires, or the like may extend from the first RFID reader antenna to the first pivot pin. Another option would be for one or more movable electrical contacts (e.g., at least generally in the form of a "pogo pin" or the like) to be biased into engagement with the first pivot pin (e.g., via one or more biasing members of any appropriate type, such as a spring), where each such electrical contact may be electrically interconnected with the first RFID reader antenna in any appropriate manner (e.g., via one or more electrical traces, wires, or the like that extend from the first RFID reader antenna to the relevant movable electrical contact). In the case where the first clamp member includes first and second RFID reader antenna sections that are spaced from each other: 1) the first pivot pin may include a first insulator section and a first pair of conductive sections, with the first insulator section being disposed between the two members of the first pair of conductive sections proceeding along the pivot axis defined by the first pivot pin (where the pivot axis coincides with the length dimension of the first pivot pin); 2) one of the members of the first pair of conductive sections (first pivot pin) may be electrically interconnected with the first RFID reader antenna section (e.g., via a first movable electrical contact that is biased into engagement with the first pivot pin); and 3) the other of the members of the first pair of conductive sections (first pivot pin) may be electrically interconnected with the second RFID reader antenna section (e.g., via a second movable electrical contact that is biased into engagement with the first pivot pin).

The power injector syringe clamp assembly may further include a second clamp member. This second clamp member may be maintained in a fixed position (e.g., a non-moving member). Another option is for the second clamp member to be a movable structure. The second clamp member may be moved into one position that is associated with the open configuration for the clamp assembly (e.g., to allow a power injector syringe to be installed in or removed from the clamp assembly). The second clamp member may be moved into another position that is associated with the closed configuration for the clamp assembly (e.g., where the first and second clamp members engage and/or are disposed in closely-spaced relation to an installed power injector syringe; where the clamp assembly restrains an installed power injector syringe in at least some manner). The first and second clamp members may be independently movable, the first and second clamp members may be simultaneously moved (e.g., via the action of a single actuator of any appropriate size, shape, configuration, and/or type), the first and second clamp member may be sequentially moved, or some combination thereof. In one embodiment, the first and second clamp members move at least generally about a common axis.

The second clamp member may be moved in any appropriate manner, including between third and fourth positions (e.g., for open and closed configurations, respectively, for the power injector syringe clamp assembly). In one embodiment, the second clamp member may utilize a pivotal motion. For instance, the second clamp member may be mounted on a second pivot pin. Power to an RFID reader antenna incorporated by the second clamp member (e.g., part of the first RFID reader antenna; a separate second RFID reader antenna) may be provided through this second pivot pin, for instance in the same manner discussed above in relation to the first pivot pin.

The first and second clamp members may be characterized as being disposed in opposing relation. For instance, the first clamp and second clamp members may disposed at a common location along the length dimension of an installed power injector syringe, with the first clamp member extending at least generally along about one-half of a circumference of the power injector syringe, and with the second clamp member extending at least generally along about the opposite half of the circumference of the power injector syringe. Other arrangements may be appropriate.

The first RFID reader antenna may be disposed entirely on the first clamp member. Another option is for a first part of the first RFID reader antenna to be disposed entirely on the first clamp member, and for a second part of the first RFID reader antenna to be disposed entirely on the second clamp member. In this instance, the first and second parts may collectively function as a single first RFID reader antenna (e.g., when the clamp assembly is in its closed configuration). The clamp assembly may also include a second RFID reader antenna, where the first RFID reader antenna is disposed entirely on the first clamp member, where the second RFID reader antenna is entirely disposed on the second clamp member, and where the first and second RFID reader antennas are autonomous or independently operable.

The power injector syringe clamp assembly may include any appropriate number of clamp members, including a single clamp member or multiple clamp members disposed in any appropriate arrangement. Each such clamp member that is in addition to the first clamp member: 1) may be a movable structure or may remain stationary; 2) may or may not include an RFID reader antenna (including where it includes all or only part of such an RFID reader antenna); and 3) including all combinations thereof.

Each RFID reader antenna that is utilized by the clamp assembly may be incorporated with a clamp member at any appropriate location. In one embodiment, an RFID reader antenna is incorporated with a surface of a clamp member that projects toward a barrel of an installed power injector syringe (e.g., when it is positioned within the clamp assembly and with the clamp assembly being in its closed configuration). In another embodiment, an RFID reader antenna is incorporated on a surface of a clamp member that projects toward a flange of an installed power injector syringe (e.g., when it is positioned within the clamp assembly and with the clamp assembly being in its closed configuration). This flange may be disposed at or near a proximal end of an installed power injector syringe, while a discharge nozzle may be disposed at or near a distal end of the power injector syringe.

Power may be provided to an RFID reader antenna incorporated by a clamp member of the power injector syringe clamp assembly in any appropriate manner. For instance and as discussed above, power may be provided to an RFID reader antenna through a pivot pin on which a clamp member may be mounted. Another option is to utilize a flexible connector. Yet another option is to dispose at least one electrical contact (of any appropriate size, shape, configuration, and/or type) within a path that a clamp member moves when changing the clamp assembly from its open configuration to its closed configuration. Each clamp member may have its own "set" of electrical contacts (where each such "set" includes at least one electrical contact). An adjacent pair of clamp members may share at least one common electrical contact. For instance, one or both clamp members of such a pair may move to dispose the clamp assembly into its closed configuration and to engage a common electrical contact or a collection of a plurality of electrical contacts.

Each RFID reader antenna of the power injector syringe clamp assembly may be of any appropriate size, shape, configuration, and/or type. Any way of integrating each RFID reader antenna with the power injector syringe clamp assembly may be utilized as well. One embodiment has an RFID reader antenna being molded into at least one clamp member of the power injector syringe clamp assembly. Another embodiment has an RFID reader antenna being printed directly on at least one clamp member of the power injector syringe clamp assembly. Yet another embodiment has an RFID reader antenna being printed on an appropriate substrate, where this substrate is then laminated or otherwise adhered to at least one clamp member of the power injector syringe clamp assembly.

The power injector syringe clamp assembly may be utilized by any appropriate power injector and may be integrated in any appropriate manner. In one embodiment, the syringe clamp assembly is mounted on a powerhead of the power injector. In another embodiment, the syringe clamp assembly is incorporated into the structure of a faceplate that in turn may be detachably mounted (e.g., by hand or without any tools) to a powerhead of a power injector. In yet another embodiment, the syringe clamp assembly is incorporated into the structure of an adapter that in turn is mounted to a powerhead of a power injector.

A second aspect of the present invention is embodied by a power injector, which includes a power injector syringe, a syringe plunger drive assembly, a first clamp member, and a first RFID reader antenna. The power injector syringe includes a syringe barrel, a plunger that is both disposed within and movable relative to the syringe barrel, and at least one RFID tag. The syringe plunger drive assembly interacts with this syringe plunger to move the same in at least one direction (e.g., to discharge fluid from the power injector syringe). The first clamp member is movable (e.g., between a first position that may be associated with an open configuration for a clamp assembly that includes the first clamp member (e.g., to allow the power injector syringe to be installed on or removed from a powerhead of the power injector), and a second position that may be associated with a closed configuration for the noted clamp assembly (e.g., where each clamp member engages and/or is disposed in closely spaced relation to the installed power injector syringe)). At least one RFID reader antenna is incorporated by the first clamp member.

Various refinements exist of the features noted in relation to the second aspect of the present invention. Further features may also be incorporated in the second aspect of the present invention as well. These refinements and additional features may exist individually or in any combination. Initially, the power injector may utilize the power injector syringe clamp assembly discussed above in relation to the first aspect, where the first clamp member of the second aspect would coincide with the first clamp member of the first aspect. This power injector syringe clamp assembly may be integrated in any appropriate manner with the power injector. In one embodiment, the syringe clamp assembly is mounted on a powerhead of the power injector. In another embodiment, the syringe clamp assembly is incorporated into the structure of a faceplate that in turn may be detachably mounted (e.g., by hand or without any tools) to a powerhead of a power injector. In yet another embodiment, the syringe clamp assembly is incorporated into the structure of an adapter that in turn is mounted to a powerhead of a power injector.

The power injector syringe may be of any appropriate size, shape, configuration, and/or type (e.g., a prefill (where the syringe is delivered to the end-use facility with fluid already loaded therein); an empty, possibly "filled" with air or any other appropriate gas or combination of gases, where the desired fluid is loaded into the syringe at the end-use facility). The power injector may provide a separate drive train section for each syringe to be installed on the power injector, where each such drive train section may be part of the syringe plunger drive assembly. A drive train section may be in the form of a threaded lead or drive screw or the like, and a ram that is mounted on the drive screw (e.g., via an intermediate threaded nut) in a manner such that a relative rotation between the drive screw and ram in one rotational direction moves the ram along the drive screw in one axial direction, and such that a relative rotation between the drive screw and ram in the opposite rotational direction moves the ram along the drive screw in the opposite axial direction.

Any appropriate drive source may provide the noted relative rotational motion for a power injector drive train section associated with a particular syringe. The power injector drive train section for each syringe could be powered by a common drive source, or each power injector drive train section could be powered by separate/independent drive sources. Each such drive source utilized by the power injector may be in the form of one or more motors of any appropriate size, shape, configuration, and/or type, such as a brushed or brushless electric motor, a hydraulic motor, a pneumatic motor, a piezoelectric motor, or a stepper motor.

Information of any type may be stored on each RFID tag being utilized by the power injector syringe. Any appropriate member of RFID tags may be utilized by the power injector syringe. Multiple RFID tags may be disposed in any appropriate arrangement. Each RFID tag associated with the syringe may be disposed at any appropriate location on the syringe. In one embodiment, an RFID tag is on the noted syringe barrel. In one embodiment, an RFID tag is on a flange that may be disposed at or near a proximal end of the syringe and that may extend outwardly from the syringe barrel. Fluid may be discharged from a distal end of the power injector syringe.

The power injector may be of any appropriate size, shape, configuration, and/or type. The power injector may utilize one or more syringe plunger drive assemblies or drivers of any appropriate size, shape, configuration, and/or type, where each such syringe plunger driver or drive assembly is capable of at least bi-directional movement (e.g., a movement in a first direction for discharging fluid (e.g., to move the syringe plunger along an axial path for a discharge stroke); a movement in a second direction for loading or accommodating a loading of fluid in the syringe (e.g., to axially retract the syringe plunger away from a syringe discharge nozzle) or so as to return to a position for a subsequent fluid discharge operation), and where each such syringe plunger driver or drive assembly may interact with its corresponding syringe plunger in any appropriate manner (e.g., by mechanical contact; by an appropriate coupling (mechanical or otherwise)) so as to be able to advance the syringe plunger in at least one direction (e.g., to discharge fluid).

The power injector may be used for any appropriate application where the delivery of one or more medical fluids is desired and in any appropriate manner (e.g., via injection into a fluid target, such as a patient), including without limitation any appropriate medical application (e.g., computed tomography or CT imaging; magnetic resonance imaging or MRI; single photon emission computed tomography or SPECT imaging; positron emission tomography or PET imaging; X-ray imaging; angiographic imaging; optical imaging; ultrasound imaging). The power injector may be used in conjunction with any component or combination of components, such as an appropriate imaging system (e.g., a CT scanner). For instance, information could be conveyed between any such power injector and one or more other components (e.g., scan delay information, injection start signal, injection rate).

Any appropriate number of syringes may be utilized with the power injector in any appropriate manner (e.g., detachably; front-loaded; rear-loaded; side-loaded), any appropriate medical fluid may be discharged from a given syringe of the power injector (e.g., contrast media, a radiopharmaceutical, saline, and any combination thereof), and any appropriate fluid may be discharged from a multiple syringe power injector configuration in any appropriate manner (e.g., sequentially, simultaneously), or any combination thereof. In one embodiment, fluid discharged from a syringe by operation of the power injector is directed into a conduit (e.g., a medical tubing set), where this conduit is fluidly interconnected with the syringe in any appropriate manner and directs fluid to a desired location (e.g., to a catheter that is inserted into a patient, for instance for injection). Multiple syringes may discharge into a common conduit (e.g., for provision to a single injection site), or one syringe may discharge into one conduit (e.g., for provision to one patient injection site), while another syringe may discharge into a different conduit (e.g., for provision to a different patient injection site). In one embodiment, each syringe includes a syringe barrel and a plunger that is disposed within and movable relative to the syringe barrel. This plunger may interface with the power injector's syringe plunger drive assembly such that the syringe plunger drive assembly is able to advance the plunger in at least one direction, and possibly in two different, opposite directions.

BRIEF DESCRIPTION OF THE FIGURES

FIG. 4A is a cutaway view of syringe mount of FIG. 2B, particularly showing first and second movable members of the syringe mount in an open position.

FIG. 4B is a cross-sectional view, taken along line 4B-4B of FIG. 4A, and also shows a coupling mechanism of a syringe plunger positioned in proximity to a plunger coupling element of a drive ram.

FIG. 5A is a cutaway view of the syringe mount of FIG. 2B, particularly showing the first and second movable members in a closed position and engaging a syringe.

FIG. 5B is a cross-sectional view, taken along line 5B-5B of FIG. 5A, and also shows the coupling mechanism on the backside of the syringe plunger engaged with the plunger coupling element of the drive ram.

FIG. 8A is a plan view of another RFID reader antenna layout that may be utilized by the power injector syringe clamp assembly of FIG. 6 (interior surface being illustrated).

FIG. 8B is a plan view of another RFID reader antenna layout that may be utilized by the power injector syringe clamp assembly of FIG. 6 (interior surface being illustrated).

FIG. 9 is a schematic of an option for providing power to an RFID reader antenna of a power injector syringe clamp assembly, using a pivot pin.

DETAILED DESCRIPTION

Figure 1A:
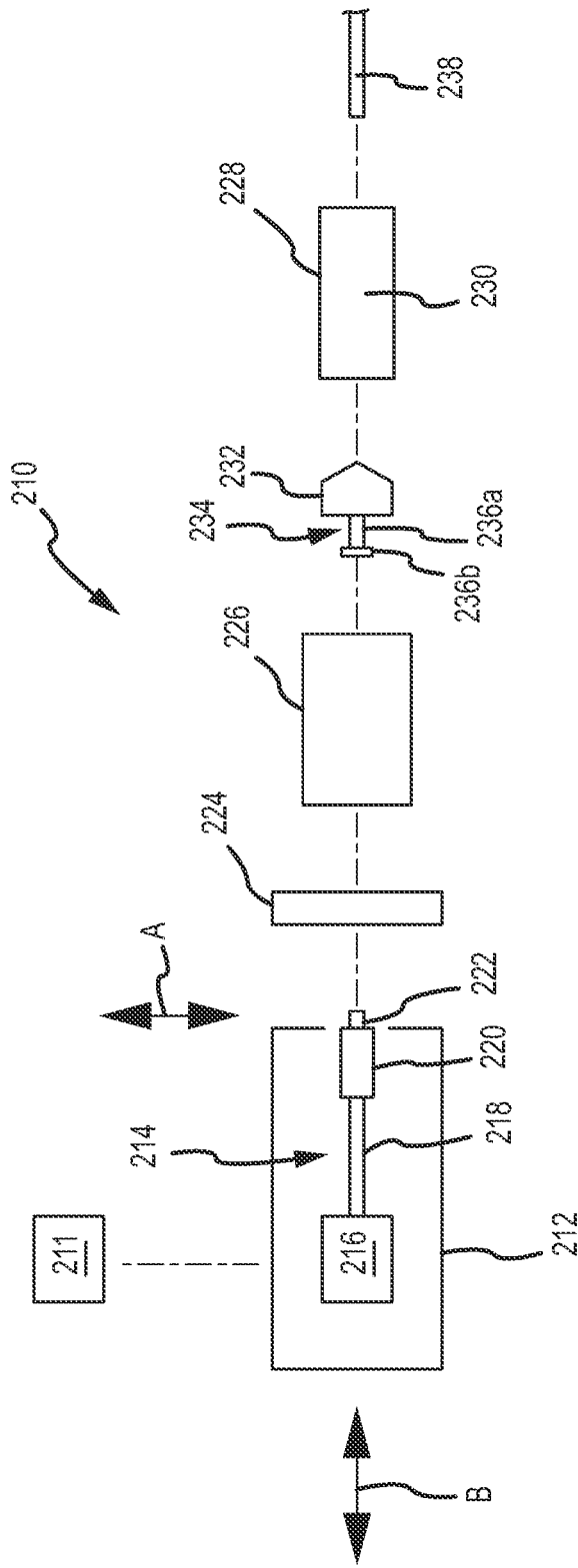
FIG. 1A is a schematic of one embodiment of a power injector.

FIG. 1A presents a schematic of one embodiment of a power injector 210 having a powerhead 212. One or more graphical user interfaces or GUIs 211 may be associated with the powerhead 212. Each GUI 211: 1) may be of any appropriate size, shape, configuration, and/or type; 2) may be operatively interconnected with the powerhead 212 in any appropriate manner; 3) may be disposed at any appropriate location; 4) may be configured to provide one or any combination of the following functions: controlling one or more aspects of the operation of the power injector 210; inputting/editing one or more parameters associated with the operation of the power injector 210; and displaying appropriate information (e.g., associated with the operation of the power injector 10); or 5) any combination of the foregoing. Any appropriate number of GUIs 211 may be utilized. In one embodiment, the power injector 210 includes a GUI 211 that is incorporated by a console that is separate from but which communicates with the powerhead 212. In another embodiment, the power injector 210 includes a GUI 211 that is part of the powerhead 212. In yet another embodiment, the power injector 210 utilizes one GUI 211 on a separate console that communicates with the powerhead 212, and also utilizes another GUI 211 that is on the powerhead 212. Each GUI 211 could provide the same functionality or set of functionalities, or the GUIs 211 may differ in at least some respect in relation to their respective functionalities.

A syringe 228 may be installed on this powerhead 212 and, when installed, may be considered to be part of the power injector 210. Some injection procedures may result in a relatively high pressure being generated within the syringe 228. In this regard, it may be desirable to dispose the syringe 228 within a pressure jacket 226. The pressure jacket 226 is typically associated with the powerhead 212 in a manner that allows the syringe 228 to be disposed therein as a part of or after installing the syringe 228 on the powerhead 212. The same pressure jacket 226 will typically remain associated with the powerhead 212, as various syringes 228 are positioned within and removed from the pressure jacket 226 for multiple injection procedures. The power injector 210 may eliminate the pressure jacket 226 if the power injector 210 is configured/utilized for low-pressure injections and/or if the syringe(s) 228 to be utilized with the power injector 210 is (are) of sufficient durability to withstand high-pressure injections without the additional support provided by a pressure jacket 226. In any case, fluid discharged from the syringe 228 may be directed into a conduit 238 of any appropriate size, shape, configuration, and/or type, which may be fluidly interconnected with the syringe 228 in any appropriate manner, and which may direct fluid to any appropriate location (e.g., to a patient).

The powerhead 212 includes a syringe plunger drive assembly or syringe plunger driver 214 that interacts (e.g., interfaces) with the syringe 228 (e.g., a plunger 232 thereof) to discharge fluid from the syringe 228. This syringe plunger drive assembly 214 includes a drive source 216 (e.g., a motor of any appropriate size, shape, configuration, and/or type, optional gearing, and the like) that powers a drive output 218 (e.g., a rotatable drive screw). A ram 220 may be advanced along an appropriate path (e.g., axial) by the drive output 218. The ram 220 may include a coupler 222 for interacting or interfacing with a corresponding portion of the syringe 228 in a manner that will be discussed below.

The syringe 228 includes a plunger or piston 232 that is movably disposed within a syringe barrel 230 (e.g., for axial reciprocation along an axis coinciding with the double-headed arrow B). The plunger 232 may include a coupler 234. This syringe plunger coupler 234 may interact or interface with the ram coupler 222 to allow the syringe plunger drive assembly 214 to retract the syringe plunger 232 within the syringe barrel 230. The syringe plunger coupler 234 may be in the form of a shaft 236a that extends from a body of the syringe plunger 232, together with a head or button 236b. However, the syringe plunger coupler 234 may be of any appropriate size, shape, configuration, and/or type.

Generally, the syringe plunger drive assembly 214 of the power injector 210 may interact with the syringe plunger 232 of the syringe 228 in any appropriate manner (e.g., by mechanical contact; by an appropriate coupling (mechanical or otherwise)) so as to be able to move or advance the syringe plunger 232 (relative to the syringe barrel 230) in at least one direction (e.g., to discharge fluid from the corresponding syringe 228). That is, although the syringe plunger drive assembly 214 may be capable of bi-directional motion (e.g., via operation of the same drive source 216), the power injector 210 may be configured such that the operation of the syringe plunger drive assembly 214 actually only moves each syringe plunger 232 being used by the power injector 210 in only one direction. However, the syringe plunger drive assembly 214 may be configured to interact with each syringe plunger 232 being used by the power injector 210 so as to be able to move each such syringe plunger 232 in each of two different directions (e.g. in different directions along a common axial path).

Retraction of the syringe plunger 232 may be utilized to accommodate a loading of fluid into the syringe barrel 230 for a subsequent injection or discharge, may be utilized to actually draw fluid into the syringe barrel 230 for a subsequent injection or discharge, or for any other appropriate purpose. Certain configurations may not require that the syringe plunger drive assembly 214 be able to retract the syringe plunger 232, in which case the ram coupler 220 and syringe plunger coupler 234 may not be desired. In this case, the syringe plunger drive assembly 214 may be retracted for purposes of executing another fluid delivery operation (e.g., after another pre-filled syringe 228 has been installed). Even when a ram coupler 222 and syringe plunger coupler 232 are utilized, it may such that these components may or may not be coupled when the ram 220 advances the syringe plunger 232 to discharge fluid from the syringe 228 (e.g., the ram 220 may simply "push on" the syringe plunger 234). Any single motion or combination of motions in any appropriate dimension or combination of dimensions may be utilized to dispose the ram coupler 222 and syringe plunger coupler 234 in a coupled state or condition, to dispose the ram coupler 222 and syringe plunger coupler 234 in an un-coupled state or condition, or both.

The syringe 228 may be installed on the powerhead 212 in any appropriate manner. For instance, the syringe 228 could be configured to be installed directly on the powerhead 212. In the illustrated embodiment, a housing 224 is appropriately mounted on the powerhead 212 to provide an interface between the syringe 228 and the powerhead 212. This housing 224 may be in the form of an adapter to which one or more configurations of syringes 228 may be installed, and where at least one configuration for a syringe 228 could be installed directly on the powerhead 212 without using any such adapter. The housing 224 may also be in the form of a faceplate to which one or more configurations of syringes 228 may be installed. In this case, it may be such that a faceplate is required to install a syringe 228 on the powerhead 212 the syringe 228 could not be installed on the powerhead 212 without the faceplate. When a pressure jacket 226 is being used, it may be installed on the powerhead 212 in the various manners discussed herein in relation to the syringe 228, and the syringe 228 will then thereafter be installed in the pressure jacket 226.

The housing 224 may be mounted on and remain in a fixed position relative to the powerhead 212 when installing a syringe 228. Another option is to movably interconnect the housing 224 and the powerhead 212 to accommodate installing a syringe 228. For instance, the housing 224 may move within a plane that contains the double-headed arrow A to provide one or more of coupled state or condition and an un-coupled state or condition between the ram coupler 222 and the syringe plunger coupler 234.

Figure 1B:
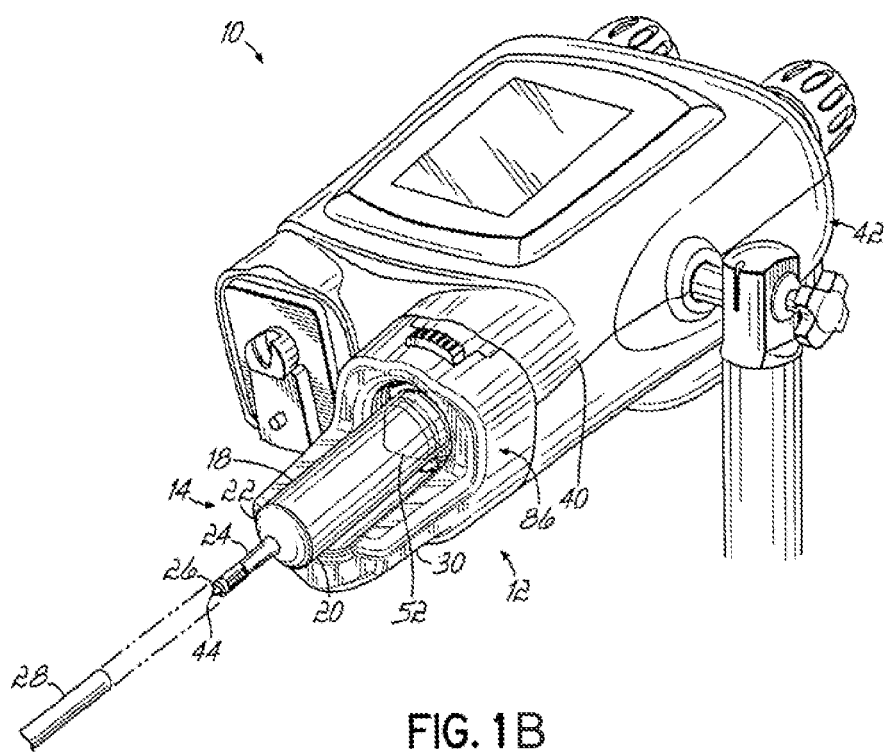
FIG. 1B is a perspective view of an injector head of an injector, having a syringe attached to a forward area thereof.

Referring to FIG. 1B, an injector 10 includes a syringe mount 12 to facilitate attachment of a syringe 14 to the injector 10 in alignment with a drive ram 16, in order to provide an injection assembly. The syringe 14 for use with the injector 10 generally includes a body 18 (which may be in the form of an exterior cylindrical barrel), which at its forward end 20, is integral with a conical front wall 22. A neck 24, terminating in a discharge tip 26, generally extends forwardly from and may be integral with the conical front wall 22. The body 18 of the syringe 14 may interface with an interior wall of a pressure jacket (not shown) or a cradle 30 when such a pressure jacket or cradle 30 is present on the injector 10. The syringe 14, as used in conjunction with the injector 10, includes a syringe mating section 32, which may be in the form of a radially outwardly extending flange 34. This flange 34 is positioned in a plane substantially perpendicular to a longitudinal axis 36 of the syringe 14 and may generally be integral with the rearward end 38 of the body 18 of the syringe 14. When the syringe 14 is associated with the injector 10, the flange 34 is positioned into and/or in contact with the syringe mount 12 located on the forward end 40 of a housing 42 of the injector 10. The syringe mating section 32 and syringe mount 12 may be utilized to facilitate operative connection of the syringe 14 to the injector 10, as will be described in greater detail below.

The discharge tip 26 of the syringe 14 has an orifice 44 defined at its remote end, which may communicate with an internal syringe cavity 46 defined within the neck 24, the conical front wall 22, and the body 18 of the syringe 14. A rearward end 48 of the cavity 46 may be defined by a generally forward facing surface 50 of a syringe plunger 52. In the illustrated embodiment, this forward facing surface 50 is substantially conical. The surface 50 may be of a slope that conforms to the slope of the interior of the conical front wall 22. The syringe plunger 52 may be snugly slidable within the body 18 of the syringe 14 such that the cavity 46 is of variable volume. Tubing (not shown) may be operatively connected to the discharge tip 26 such that fluid can be expressed from the syringe 14 through the tubing.

Referring now to FIGS. 1, 4B, and 5B, the syringe plunger 52 can be seen more clearly within the body 18 of the syringe 14. When the syringe 14 is attached to the injector 10, the syringe plunger 52 is preferably located proximal to and in substantial alignment with the drive ram 16 of the injector 10. The drive ram 16 is driven by a motor (not shown) to move in a forward or rearward motion along its longitudinal axis 54 to deploy the drive ram 16, and thus to responsively deploy the syringe plunger 52 in a forward or rearward motion along the longitudinal axis 36 of the syringe 14, to inject fluid into a patient or to fill the syringe 14 with fluid, respectively. For example, one may load a prefilled syringe into the injector 10 and, by deploying the plunger 52 in a forward direction, may thereby expel fluid from the syringe 14. In so doing, the fluid may be injected into the patient. Alternatively, an empty syringe may be loaded into the injector 10 while the syringe plunger 52 may be located at or near its forward-most position. Thereafter, fluid (e.g., contrast media) may be loaded into the syringe 14 by operatively connecting the syringe 14 to a source of fluid and retracting the syringe plunger 52 in a rearward direction in order to draw fluid into the syringe 14.

The injector 10 may be designed to accommodate prefilled syringes or empty syringes of varying volumes. For example, the injector 10 may be adapted to receive 125 ml prefilled syringes (e.g., Ultraject® syringe commercially available from Mallinckrodt Inc. of St. Louis, Mo.). Such syringes may be used for injecting contrast media into a patient. These 125 ml syringes may be prefilled with any of a range of appropriate amounts of fluid, such as 50 ml, 75 ml, 100 ml, 125 ml, or other amount. Additionally, the injector 10 may accommodate an empty syringe of any of a variety of sizes (e.g., 50 ml, 75 ml, 100 ml, 125 ml, 130 ml, etc.).

Referring now to FIGS. 2A-5B, one embodiment of a syringe mount 12 is shown. The syringe mount 12 includes a movable actuator 56 including a wall member 58 defining an orifice 60, and at least a first movable member 62 operatively coupled to the actuator 56 and responsively movable therewith. More specifically, the syringe mount 12 of the illustrated embodiment includes first and second movable members 62, 64 that are operatively coupled to the wall member 58 of the actuator 56. The first and second movable members 62, 64 include first and second pins 66, 68 operatively connected thereto. The first pin 66 is operatively coupled near a first end 70 of the first movable member 62, and the second pin 68 is operatively coupled near a first end 72 of the second movable member 64. The first and second pins 66, 68 are received in at least one slot 74 defined in the wall member 58 of the actuator 56, to couple the first and second movable members 62, 64 thereto. The actuator 56 is disposed proximally of the first and second movable members 62, 64. Further, the first and second members 62, 64 may include first and second rods 67, 69 projecting rearwardly therefrom. These first and second rods 67, 69 may confront and move along the outer contour of the wall member 58 of the actuator 56, as the first and second movable members 62, 64 move between open and closed positions.

The slot 74 is defined by the wall member 58 of the actuator 56 at a base portion 76 thereof. The first and second pins 66, 68 are movable (e.g., slidable and optionally rotatable) within the slot 74. Each of the first and second pins 66, 68 can move from a position proximal to the center 78 of the slot 74, to positions near first and second terminal ends 80, 82 of the slot 74. The first and second pins 66, 68 do not both move on one side of the slot 74. Rather, the first pin 66 is adapted to move within one portion of the slot 74, and the second pin 68 is adapted to move within another portion of the slot 74. In particular, in the illustrated embodiment, a base portion 76 of the wall member 58 includes an opening 84 having a top portion thereof in a shape at least generally similar to a "V." The first and second pins 66, 68 are disposed in the "V" portion of this opening 84. When the first and second pins 66, 68 are positioned near the intersection of the two legs of the "V," the first and second movable members 62, 64 are in an open position (see FIG. 4A). When the first and second pins 66, 68 are positioned near the first and second terminal ends 80, 82 of the "V," the first and second movable members 62, 64 are in a closed position (see FIG. 5A). While the slot 74 of the illustrated embodiment is shown and described here as generally having a "V" shape, it will be recognized by those skilled in the art that such a "V" shape is not necessary, and any other shape can be used that allows the first and second movable members 62, 64 to move sufficiently within a slot to operatively connect a syringe to an injector 10. For example, the slot 74 may have a "U" or "C" shape. Further, those skilled in the art will recognize that more than one slot may be used. For example, two slots forming a "V" shape proximal to the base 76 of the wall member 58 can receive the first and second pins 66, 68 near the point of the "V." Again, those skilled in the art will recognize that the slots do not necessarily have to be in the shape of a "V."

Figure 2B:
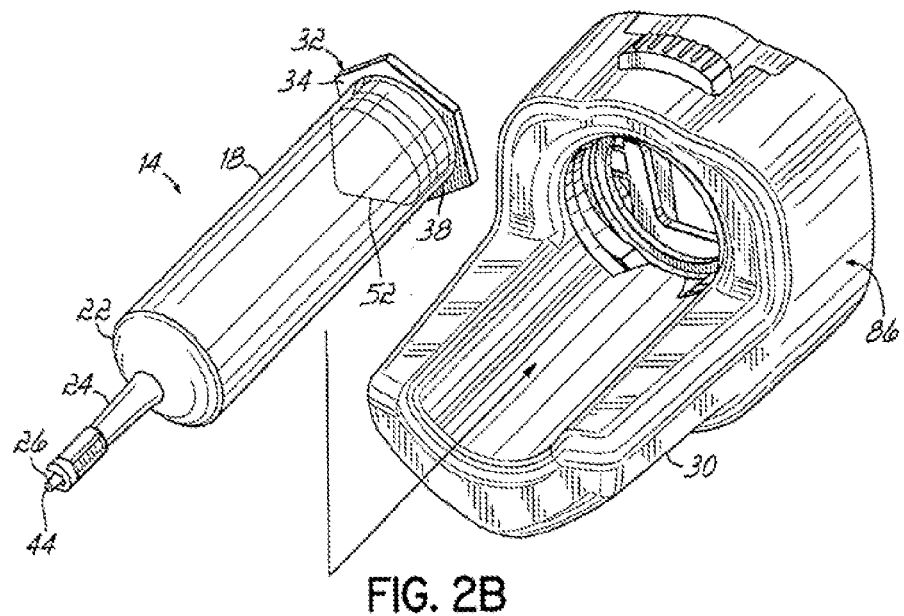
FIG. 2B is a perspective view of the syringe mount of FIG. 2A in an assembled condition.
Figure 2A:
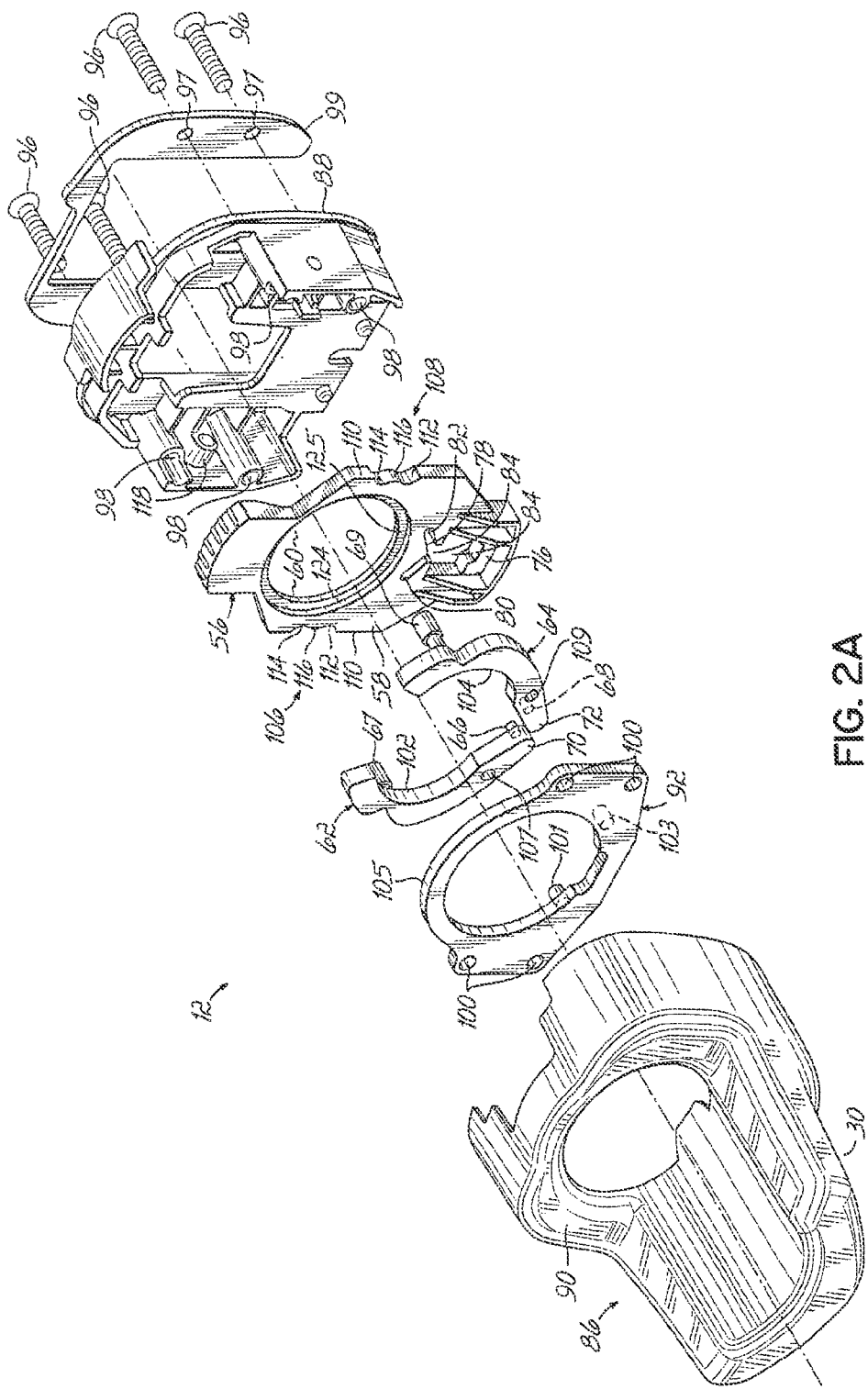
FIG. 2A is an exploded view of one exemplary embodiment of a syringe mount.
Figure 3B:
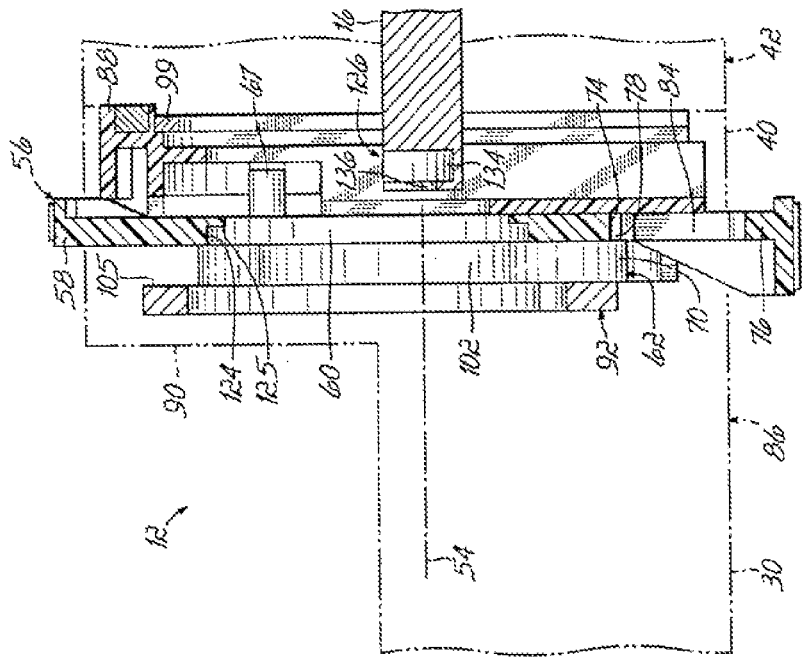
FIG. 3B is a cross-sectional view, taken along line 3B-3B of FIG. 3A.
Figure 3A:
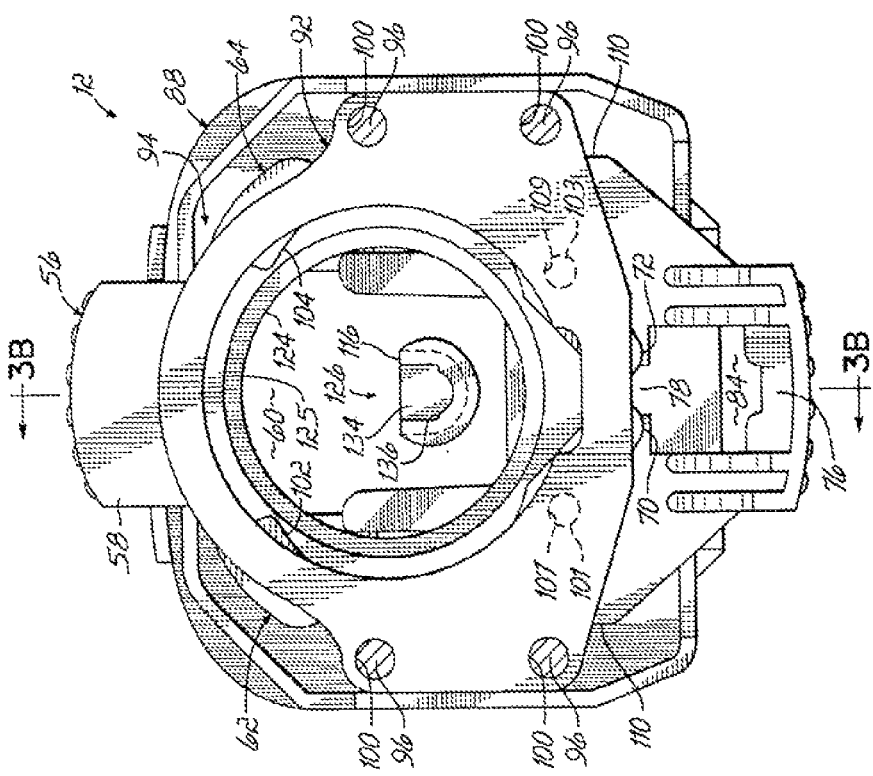
FIG. 3A is a cutaway view of the syringe mount of FIG. 2B, particularly showing an actuator of the syringe mount.

As can be seen from FIGS. 2A-5B, the actuator 56 and the first and second movable members 62, 64 of the syringe mount 12 are held within a face plate 86 of the housing 42 of the injector 10 (additional views of the face plate may be seen in FIGS. 6-12). Referring particularly to FIG. 2A, the face plate 86 includes a proximal wall portion 88, a distal wall portion 90, a cradle 30 extending distally from the distal wall portion 90, and a coupling plate 92. The first and second movable members 62, 64 are located between the coupling plate 92 and the wall member 58 of the actuator 56, and all three components are then contained within an interior cavity 94 of the face plate 86, formed between the proximal wall portion 88 and distal wall portion 90. The actuator 56 and the first and second movable members 62, 64 are movable within the interior cavity 94. The coupling plate is preferably substantially immobile relative to the proximal and distal wall portions of the face plate 86, as it is preferably fixed to at least one of the proximal and distal wall portions 88, 90. In the illustrated embodiment, this fixing occurs through the use of screws 96, which extend through orifices 97 in a rear plate 99, orifices 98 in the proximal wall portion 88, orifices 100 in the coupling plate 92, and are received in orifices (not shown) in the distal wall portion 90.

The coupling plate 92 includes first and second pivoting shafts 101, 103 projecting from a proximal surface 105 thereof. These first and second pivoting shafts 101, 103 are received in first and second shaft openings 107, 109 defined in the first and second movable members 62, 64, respectively. As such, the first and second movable members 62, 64 are able to exhibit a pivoting motion about the corresponding first and second pivot shafts 101, 103. Stated another way, the first and second movable members 62, 64 are coupled with corresponding the first and second pivoting shafts 101, 103 in a manner such that the movable members 62, 64 can pivot thereabout. The first and second pivoting shafts 101, 103 thus may be said to provide pivot points for the first and second movable members 62, 64.

To initiate loading of the syringe 14 into the syringe mount 12, the flange 34 at the rearward end 38 of the syringe 14 may be passed through an aperture in each of the distal wall portion 90 of the syringe mount 12 and the coupling plate 92 and may be received into the orifice 60 defined in the actuator 56. While the rearward end 38 of the syringe 14 is located in the orifice 60, the syringe 14 may be moved in a first direction substantially perpendicular to the longitudinal axis 54 of the drive ram 16 of the injector 10. Herein, this direction will be referred to as a "downward" direction (as the motion is down relative to the injector 10). However, it will be recognized by those skilled in the art that the motion does not have to be "downward," but that the components of the syringe mount 12 can be configured such that motion in other directions can effect appropriate engagement of the syringe 14 (including, but not limited to, "upward" movement, "side-to-side" movement, or any other appropriate, substantially perpendicular movement such that the longitudinal axis 36 of the syringe 14 is moved into a substantially coaxial relationship with the longitudinal axis 54 of the drive ram 16). This downward motion, in turn, responsively moves the actuator 56 in the downward direction. The motion of the actuator 56 in the downward direction causes each of the first and second pins 66, 68 to move to the corresponding first and second ends 80, 82 of the slot 74 defined in the base portion 76 of the wall member 58. This movement of the pins 66, 68 occurs because the first and second movable members 62, 64 cannot move in the downward direction due to the first and second pivoting shafts 101, 103 of the fixed coupling plate 92 being located within the first and second shaft openings 107, 109 of the first and second movable members 62, 64. Thus, as the actuator 56 moves in the downward direction, the first and second pins 66, 68 move within the slot 74 to the first and second terminal ends 80, 82 thereof. Because the first and second movable members 62, 64 cannot move downwardly, they instead pivot about the pivot points provided by the first and second pivoting shafts 101, 103. In other words, the first and second movable members 62, 64 rotate about the corresponding first and second pivoting shafts 101, 103 at the respective first and second shaft openings 107, 109. As such, the first and second movable members 62, 64 pivot to engage (e.g., substantially, circumferentially envelop) the rearward end 38 of the syringe 14 (see FIG. 5A). Since the flange 34 of the syringe 14 is located within the actuator 56 during this pivoting movement of the movable members 62, 64, the first and second movable members 62, 64 engage the body 18 of the syringe 14 (rather than the flange 34). In embodiments where the movable members 62, 64 are designed such that this engagement with the body 18 of the syringe 14 may be characterized as a substantial enveloping of the body 18, it may be said that this type of engagement allows for greater coverage of the syringe 14 than found in prior syringe mounts, and thus, potentially allows the syringe 14 to withstand greater injection pressures.

In the illustrated embodiment, the first and second movable members 62, 64 are opposite one another and are positioned about the longitudinal axis 54 of the drive ram 16. Further, the first and second movable members 62, 64 each have an arcuate face 102, 104. These arcuate faces 102, 104 are shown as being diametrically opposite one another and located exterior to the body 18 of the syringe 14. When the syringe 14 is properly engaged with the syringe mount 12 of the injector 10, the first and second movable members 62, 64 of the syringe mount 12 are in contact with the side surface of the exterior body 18 of the syringe 14 to hold the syringe 14 in place and in alignment with the drive ram 16 of the injector 10.

In some embodiments, the arcuate faces 102, 104 of the movable members 62, 64 may bear one or more types of engagement enhancing features (e.g., grooves, bumps, indentations, ridges, teeth, combinations thereof, and the like) to improve the ability of the movable members 62, 64 to grip and/or hold the syringe 14. In some embodiments, a grip enhancing coating (e.g., Santoprene® elastomer) may be applied to the arcuate faces 102, 104 of the movable members 62, 64 to facilitate gripping/holding of the syringe 14.

The pivotal movement of the first and second movable members 62, 64 alters the distance between the arcuate faces 102, 104 as they pivot toward and away from one another. In the illustrated embodiment, the first and second movable members 62, 64 are each movable. In some embodiments, it is possible to use a single movable member disposed in spaced relation to an immobile member (e.g., arcuate stop or abutment) toward which the single movable member may be moved.

In some embodiments, first and second movable members 62, 64 are not necessary for appropriate syringe engaging function. In such embodiments, a single gripping member may be used to engage the syringe 14, thereby operatively connecting the syringe 14 to the injector 10. In such embodiments, the single movable member should cover enough of the circumference of the syringe 14, when in contact with the body 18, to hold the syringe 14 against the injector 10. In such embodiments, each arm extending from a center point of the movable member may have a degree of elasticity such that the arms may splay outwardly and inwardly to allow for insertion and/or removal of the syringe 14.

The wall member 58 of the actuator 56 is shown as having a peripheral side surface 110 that includes a first undulating contour 106 and a second undulating contour 108. As shown, the second undulating contour 108 is positioned substantially opposite the first undulating contour 106. Each of these first and second undulating contours 106, 108 includes a first valley 112, a second valley 114, and a ridge 116 disposed therebetween. When positioned within the syringe mount 12 of the injector 10, these first and second undulating contours 106, 108 are confronted by first and second projections 118, 120 (see FIGS. 2A and 5A), which are adapted to ride along the surface of the first and second undulating contours 106, 108 as the actuator 56 is moved between the first and second positions. In the illustrated embodiment, the first and second projections 118, 120 are coupled to the proximal wall portion 88 of the face plate 86, and are spring-biased in a direction toward each of the first and second undulating contours 106, 108. The interaction of the first and second detents 118, 120 and first and second undulating contours 106, 108 assist in maintaining the actuator 56 in either the first or second position until a user desires to move the actuator 56 to either load or unload the syringe 14. In some embodiments, the first and second pins 66, 68 may include bias springs associated with each of the first and second movable members 62, 64. In such embodiments, one end of each of the bias springs may be in contact with its respectively associated movable member, and the opposite end of each bias spring may seat or bear against portions of the housing 42 (or face plate 86) of the injector 10. In some embodiments, at least a portion of these bias springs may be disposed about the pins 66, 68, which form the pivot axes of the first and second movable members 62, 64.

To load a syringe 14 into the injector 10, the syringe 14 is positioned relative to the wall member 58 of the actuator 56 such that the flange 34 at the rearward end 38 of the syringe 14 is received within the orifice 60 of the wall member 58 such that at least one contact point 122 on the periphery of the flange 34 contacts or can be brought into contact with a peripheral surface 124 defining the orifice 60. More specifically, the flange 34, in certain embodiments, may be received by a recess 125 in the actuator 56. The actuator 56 is shown in FIG. 4A as being in the first position, such that the first and second movable members 62, 64 are in the open position. Also in this first position, the first and second projections 118, 120 are in contact with the first valleys 112 of the corresponding first and second undulating contours 106, 108. The force of the spring bias of the first and second projections 118, 120 at least assists in preventing the wall member 58 of the actuator 56 from moving unassisted to the second position. Further, the drive ram 16 of the injector 10 is preferably positioned such that a plunger coupling mechanism 126 is aligned with a coupling mechanism 128 extending from a rearward face of the syringe plunger 52 (see FIG. 4B).

A user then applies a force to the syringe 14 in a direction substantially perpendicular to, and towards, the longitudinal axis 54 of the drive ram 16. The flange 34 of the syringe 14, contacting the peripheral surface 124 of the wall member 58, is utilized to force the wall member 58 of the actuator 56 to responsively move in a direction substantially perpendicular to the longitudinal axis 54 of the drive ram 16. Enough force is applied to overcome the spring-bias of the first and second projections 118, 120, such that the actuator 56 moves from the first position to the second position. As this occurs, the first and second projections 118, 120 ride along the first and second undulating contours 106, 108 from the first valleys 112, along the ridges 116, and into the second valleys 114. The first and second projections 118, 120 may then be utilized to at least assist in maintaining the wall member 58 in the second position shown in FIG. 5A.

The movement of the wall member 58 from the first position to the second position cooperatively moves the slot 74 of the wall member 58 in a direction substantially perpendicular to the longitudinal axis 54 of the drive ram. And thus, the slot 74 moves relative to the first and second pins 66, 68, thereby causing the first and second pins 66, 68 to move relative to and within the slot 74. More specifically, in the illustrated embodiment, the first and second pins 66, 68 move within the V-shaped slot from a position proximal to the point of the "V," to positions proximal to the terminal ends of each leg of the "V" (from the position shown in FIG. 4A, to the position shown in FIG. 5A). This movement causes a responsive pivotal movement of the first and second movable members 62, 64 from the open position to the closed position such that the rearward end 38 of the syringe 14 is engaged by the first and second movable members 62, 64. In particular, as the actuator 56 moves in the downward direction, the first and second pins 66, 68 move within the slot 74 to the first and second terminal ends 80, 82 thereof. Because the first and second movable members 62, 64 cannot move downwardly, they instead pivot about the pivot points provided by the first and second pivoting shafts 101, 103. In other words, the first and second movable members 62, 64 rotate about the first and second pivoting shafts 101, 103 at the first and second shaft openings 107, 109, respectively.

As the wall member 58 is moved from the first position to the second position, and the syringe 14 moves with the wall member 58 from a position not engaged by the movable members 62, 64 to a position engaged by the movable members 62, 64, the coupling mechanism 128 at the rearward end 38 of the syringe plunger 52 moves from a position not engaged with the plunger coupling mechanism 126 of the drive ram 16 to a position engaged with the plunger coupling mechanism 126 of the drive ram 16. In the illustrated embodiment (see FIGS. 4B and 5B), when the flange 34 of the syringe 14 is aligned with the orifice 60 defined by the wall member 58, the syringe plunger 52 within the syringe 14 is preferably positioned such that the coupling mechanism 128 on the rearward face of the syringe plunger 52 is aligned with the plunger coupling mechanism 126 of the drive ram 16. The coupling mechanism 128 of the illustrated syringe plunger 52 is a projection 128 extending from the rearward face of the syringe plunger 52. This projection 128 may be characterized as exhibiting a "T" shape having a stem portion 130 (parallel to the longitudinal axis 36 of the syringe 14) topped by a cap portion 132 (transverse to the longitudinal axis of the syringe 14). As the wall member 58 is moved from the first position to the second position, the cap portion 132 of the coupling mechanism 128 may be received by the plunger coupling mechanism 126, which in the illustrated embodiment, is a slot 134 formed in the forward end of the drive ram 16.

A slot 134 is defined in the forward end of the drive ram 16 in a shape to receive the coupling mechanism 128 of the syringe 14, and particularly the cap portion 132 thereof. A cross-section of the plunger coupling element 126 is shown as exhibiting a J-shape (having a slot within a hook portion of the "J" configured to receive the cap portion 132), such that when the syringe plunger 52 is engaged with the drive ram 16, the distal end 136 of the "J" shape is positioned distally of a part of the cap portion 132 of the coupling mechanism 128. Thus, when the syringe 14 is initially inserted into the actuator 56 (in the first position), the cap portion 132 of the coupling mechanism 128 is "above" the plunger coupling element 126 of the drive ram 16. However, as the actuator 56 is moved to the second position, the cap portion 132 of the coupling mechanism 128 is moved to be positioned proximally of the distal end 136 of the plunger coupling mechanism 126 of the drive ram 16. Once engaged, an injection procedure may be run, such as by translating the drive ram 16 forward along its longitudinal axis 54 to dispense a fluid, such as contrast media, from the syringe 14. While the slot 134 and extension 128 of the illustrated embodiment have shapes referred to herein as "J" and "T," respectively, it will be recognized by those of skill in the art that any shape that facilitates coupling may be used. Additionally, while the illustrated embodiment depicts first a coupling mechanism 128 and plunger coupling mechanism 126 that result in a passive coupling, those of skill in the art will recognize that coupling mechanisms and plunger coupling mechanisms that result in an active coupling (one which involves some degree of positive gripping) may be used.

As described previously, the syringe mount 12 allows for the syringe 14 to be removed from the face plate 86 and/or forward end 40 of the injector 10, when the drive ram 16 of the injector 10 is at any position. It does not require the drive ram 16 to be returned to a "home" position before detaching the syringe 14 from the injector 10. Thus, during an injection procedure, the translation of the drive ram 16 may be stopped while the drive ram 16 is in an extended position from the front face place 86 of the injector 10. A user can then grip the syringe 14 and move it in an upward direction, thereby overcoming the spring-biased force of the first and second projections 118, 120 to cause the actuator 56 to move from the second position to the first position. As this occurs, the first and second projections 118, 120 ride along the first and second undulating contours 106, 108 from the second valleys 114, over the ridges 116, and into the first valleys 112. Simultaneously, the first and second pins 66, 68 of the first and second movable members 62, 64 will move within the V-shaped slot of the wall member 58 from a position near the terminal ends 80, 82 of the arms of the V to a position near the point of the V. This causes the first and second movable members 62, 64 to pivot from the closed position to the open position by pivoting about the pivot points created by the interaction of the first and second pivoting shafts 101, 103 with the first and second shaft openings 107 109. Due to the positioning of the flange 34 at the rearward end 38 of the syringe 14 within the orifice 60 of the actuator 56, the actuator 56 allows for enough vertical syringe movement for the T-shaped coupling mechanism on the rearward face of the syringe 14 to clear the slot on the forward end of the drive ram 16, thereby allowing removal of the syringe 14 from the injector 10.

The power injectors 210, 10 of FIGS. 1A and 1B each may be used for any appropriate application, including without limitation for medical imaging applications where fluid is injected into a subject (e.g., a patient). Representative medical imaging applications for the power injectors 210, 10 include without limitation computed tomography or CT imaging, magnetic resonance imaging or MRI, SPECT imaging, PET imaging, X-ray imaging, angiographic imaging, optical imaging, and ultrasound imaging. The power injectors 210, 10 each could be used alone or in combination with one or more other components. The power injectors 210, 10 each may be operatively interconnected with one or more components, for instance so that information may be conveyed between the power injector 210, 10 and one or more other components (e.g., scan delay information, injection start signal, injection rate).

Any number of syringes may be utilized by each of the power injectors 210, 10, including without limitation single-head configurations (for a single syringe) and dual-head configurations (for two syringes). In the case of a multiple syringe configuration, each power injector 210, 10 may discharge fluid from the various syringes in any appropriate manner and according to any timing sequence (e.g., sequential discharges from two or more syringes, simultaneous discharges from two or more syringes, or any combination thereof). Multiple syringes may discharge into a common conduit (e.g., for provision to a single injection site), or one syringe may discharge into one conduit (e.g., for provision to one injection site) while another syringe may discharge into a different conduit (e.g., for provision to a different injection site). Each such syringe utilized by each of the power injectors 210, 10 may include any appropriate fluid, for instance contrast media, a radiopharmaceutical, saline, and any combination thereof. Each such syringe utilized by each of the power injectors 210, 10 may be installed in any appropriate manner (e.g., rear-loading configurations may be utilized; front-loading configurations may be utilized; side-loading configurations may be utilized).

Figure 6:
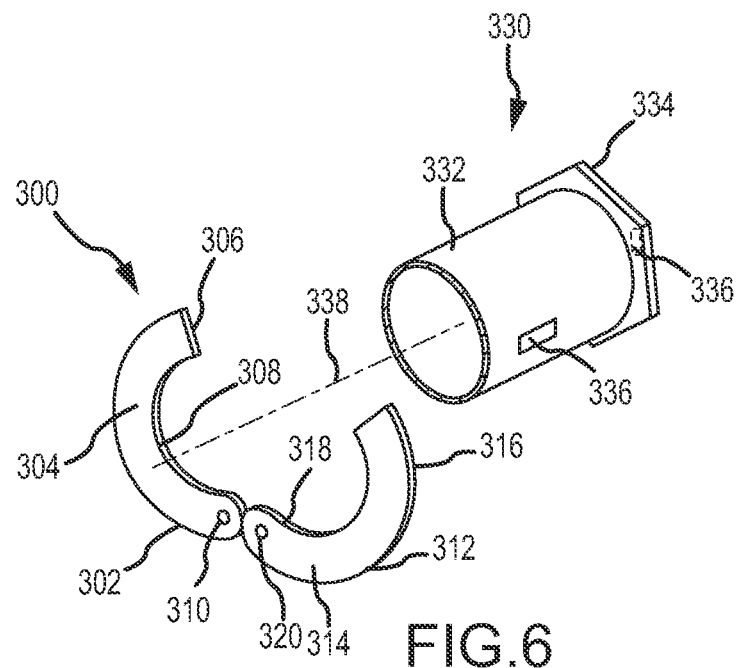
FIG. 6 is a perspective schematic of one embodiment of a power injector syringe clamp assembly, along with a proximal portion of a representative power injector syringe.

FIG. 6 is a perspective view of one embodiment of a power injector syringe clamp assembly 300, which may be used by the power injector 10 of FIG. 1B (replacing the members 62, 64 of the syringe mount 12 within the faceplate 86, shown in FIG. 2A), as well as any other appropriate power injector. Generally, the clamp assembly 300 may be used to hold or retain a power injector syringe 330 on a powerhead of the corresponding power injector. Although the clamp assembly 300 could exert a compressive force on the power injector syringe 330, such may not be required in all instances. Instead, one or more portions of the clamp assembly 300 could be disposed in closely spaced relation to the power injector syringe 330, one or more portions of the clamp assembly 300 could simply be disposed in interfacing relation with the power injector syringe 330, or both. In any case, the clamp assembly 300 includes at least one RFID reader antenna for communicating with one or more RFID tags 336 on the power injector syringe 330. Any appropriate number of RFID reader antennas may be utilized by the clamp assembly 300, with each RFID reader antenna being of any appropriate size, shape, configuration, and/or type (e.g., of any appropriate layout or pattern). Any appropriate way of providing power to an RFID reader antenna of the clamp assembly 300 may be utilized. Any appropriate way of incorporating one or more RFID reader antennas with the clamp assembly 300 may be utilized (e.g., separately mounting one or more RFID reader antennas to the clamp assembly 300; integrating one or more RFID reader antennas into the structure of the clamp assembly 300; and including any combination thereof).

Figure 7:
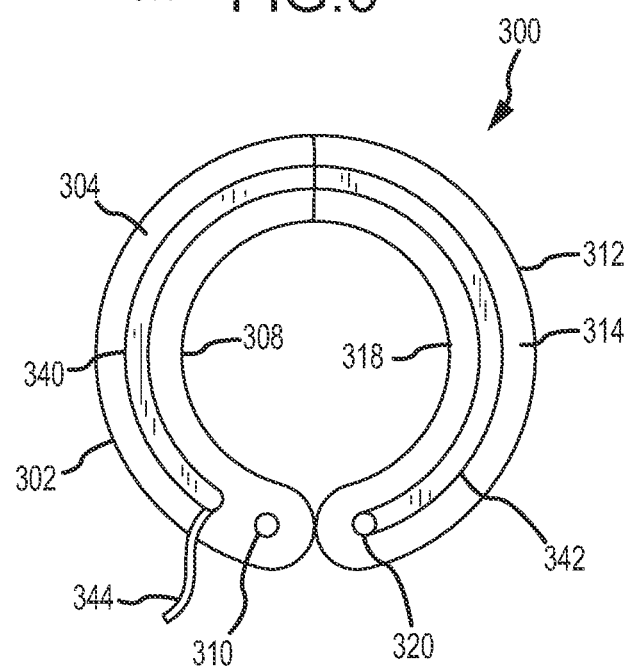
FIG. 7 is a plan view of one RFID reader antenna layout that may be utilized by the power injector syringe clamp assembly of FIG. 6 (end surfaces being illustrated).

Various integrations of an RFID reader antenna by the clamp assembly 300 will be discussed below in relation to FIGS. 7-10. Referring first to FIG. 7, there the clamp assembly 300 includes a first clamp member 302 and a second clamp member 312. The first clamp member 302 and the second clamp member 312 may be characterized as being disposed in opposing relation. In the illustrated embodiment, each clamp member 302, 312 is disposed outwardly from different portions of the syringe barrel 332 of the power injector syringe 330, but at the same location along the length dimension of the power injector syringe 330 (the length dimension coinciding with an axis 338). The first clamp member 302 includes oppositely disposed end surfaces 304, 306, along with an inner or interior surface 308. The end surface 306 would project toward or face a flange 334 of the power injector syringe 330 when positioned within the clamp assembly 300 and with the clamp assembly 300 being in a closed configuration (a representative closed configuration being shown in FIG. 7). That is, the syringe flange 334 would be disposed behind the clamp assembly 300 in the view shown in FIG. 6. In any case, the inner surface 308 would project toward or face the barrel 332 of the power injector syringe 330 when positioned within the clamp assembly 300 and with the clamp assembly 300 being in its closed configuration. A first pivot pin 310 pivotally interconnects the first clamp member 302 with the powerhead of the power injector that is incorporating the clamp assembly 300.

The second clamp member 312 includes oppositely disposed end surfaces 314, 316, along with an inner or interior surface 318. The end surface 316 would project toward or face the syringe flange 334 of the power injector syringe 330 when positioned within the clamp assembly 300 and with the clamp assembly 300 being in a closed configuration. That is, the syringe flange 334 would be disposed behind the clamp assembly 300 in the view shown in FIG. 6. In any case, the inner surface 318 would project toward or face the barrel 332 of the power injector syringe 330 when positioned within the clamp assembly 300 and with the clamp assembly 300 being in its closed configuration. A second pivot pin 320 pivotally interconnects the first clamp member 312 with the powerhead of the power injector that is incorporating the clamp assembly 300.

The flange 334 of the power injector syringe 330 may be characterized as being located at or on a proximal end of the power injector syringe 330 (e.g., an oppositely disposed distal end of the power injector syringe 330 may accommodate a fluid discharge from the power injector syringe 330; the flange 334 being located similarly to the flange 34 of the syringe 14 shown in FIG. 1B). At least one RFID tag 336 is disposed on the power injector syringe 330. Each RFID tag 336 may be of any appropriate size, shape, configuration, and/or type, may be fabricated in any appropriate manner, may be encoded with any appropriate information, and may be disposed at any appropriate location on the power injector syringe 330. Any appropriate number of RFID tags 336 may be disposed on the power injector syringe 330, and multiple RFID tags 336 may be disposed in any appropriate arrangement. One or more RFID tags 336 could be disposed on the syringe barrel 332, one or more RFID tags 336 could be disposed on the flange 334 of the power injector syringe 330, or both.

The illustrated embodiment of the clamp assembly 300 allows each of the first clamp member 302 and the second clamp member 312 to move between at least two general positions to define open and closed configurations for the clamp assembly 300. Each of the first clamp member 302 and the second clamp member 312 may be moved along any appropriate path or combination of paths to define open and closed configurations for the clamp assembly 300. Any appropriate way of actuating the clamp assembly 300 into each of its open and closed configurations may be utilized. In one embodiment, a single actuator of any appropriate size, shape, configuration, and/or type (e.g., actuator 56) simultaneously pivots the first clamp member 302 and the second clamp member 312 about their respective pivot pins 310, 320. It should be appreciated that separate actuators could be provided for each of the first clamp member 302 and the second clamp member 312. It should also be appreciated that one of the first clamp member 302 and the second clamp member 312 could actually be maintained in a stationary or fixed position (at least relative to the other clamp member 302, 312), while the other is moved in any appropriate manner to provide the open and closed configurations for the clamp assembly 300 (not shown).

FIG. 7 illustrates one option for integrating at least one RFID reader antenna with the clamp assembly 300. A first RFID reader antenna section 340 is disposed on the end surface 304 of the first clamp member 302 (end surface 306 being another option—not shown), while a second RFID reader antenna section 342 is disposed on the end surface 314 of the second clamp member 312 (end surface 316 being another option—not shown). The first RFID reader antenna section 340 and the second RFID reader antenna section 342 each could be autonomous or independently operable (e.g., fully functional) RFID reader antennas. Alternatively, the first RFID reader antenna section 340 and the second RFID reader antenna section 342 may collectively define a single RFID reader antenna (at least when the clamp assembly 300 is in the closed configuration shown in FIG. 7). Any appropriate layout may be utilized for each of the first RFID reader antenna section 340 and the second RFID reader antenna section 342.

Two options for providing power to an RFID reader antenna integrated with the clamp assembly 300 are also illustrated by FIG. 7. Power to the RFID reader antenna section 340 is provided by a flex connector 344 of any appropriate size, shape, configuration, and/or type. Power to the second RFID reader antenna section 342 is provided though the second pivot pin 320, which would therefore be formed from an electrically conductive material or combination of materials.

Another layout for an RFID reader antenna is illustrated in FIG. 8A. Here an RFID reader antenna section 350 is disposed on an inner surface 308/318 of the first/second clamp member 302/312 (the surface of the clamp member 302/312 that projects toward or faces the syringe barrel 332 when the power injector syringe 330 is positioned within the clamp assembly 300). Although the first/second pivot pins 310/320 are not shown in FIG. 8A, the first/second pivot axis 311/321 is shown in FIG. 8A (the axis 311/321 about which the respective first/second clamp member 302/312 moves). The RFID reader antenna section 350 functions itself as an RFID reader antenna in the illustrated embodiment, although it could be configured to collectively define an RFID reader antenna with another RFID reader antenna section on the other clamp member 302/312 of the clamp assembly 300 (not shown).

FIG. 8B shows another possible layout for an RFID reader antenna on the power injector syringe clamp assembly 300 of FIG. 6. Here a first RFID reader antenna section 360 and a second RFID reader antenna section 362 are each disposed on an inner surface 308/318 of the first/second clamp member 302/312 (the surface of the clamp member 302/312 that projects toward or faces the syringe barrel 332 when the power injector syringe 330 is positioned within the clamp assembly 300). Although the first/second pivot pins 310/320 are not shown in FIG. 8B, the first/second pivot axis 311/321 is shown in FIG. 8B (the axis 311/321 about which the respective first/second clamp member 302/312 moves). The RFID reader antenna sections 360, 362 could each function as an RFID reader antenna in the illustrated embodiment. Each RFID reader antenna section 360, 362 could collectively define an RFID reader antenna with another RFID reader antenna section on the other clamp member 302/312 of the clamp assembly 300 (such that the clamp assembly 300 would include two, separate RFID reader antennas). Finally, each RFID reader antenna section 360, 362 could be part of a single RFID reader antenna for the clamp assembly 300, including where one or more RFID reader antenna sections are disposed on the other clamp member 302/312.

Two ways of providing electrical power to an RFID reader antenna on the clamp assembly 300 were discussed above in relation to FIG. 7. Additional options are presented in FIGS. 9 and 10. In FIG. 9, a pivot pin 370 is configured to provide separate electrical connections to the pair of spaced RFID reader antenna sections 360, 362 shown in FIG. 8B. The pivot pin 370 for the clamp member 302/312 includes a first conductive section 372 and a second conductive section 376 that are separated by an intermediate insulator section 374. A pair of movable and electrically conductive pins 378 are spaced from each other and biased into contact with the pivot pin 370 in any appropriate manner (e.g., using a spring or the like—not shown). One conductive pin 378 engages the first conductive section 372 of the pivot pin 370, while the other conductive than 378 engages the second conductive section 376 of the pivot pin 370. Each conductive pin 378 is also in electrical contact with its own conductor 380, at least when the conductive pins 378 are in contact with the pivot pin 370. One conductor 380 extends to or is otherwise in electrical communication with the first RFID reader antenna section 360, while the other conductor 380 extends to or is otherwise in electrical communication with the second RFID reader section 362 (see FIG. 8B).

Figure 10:
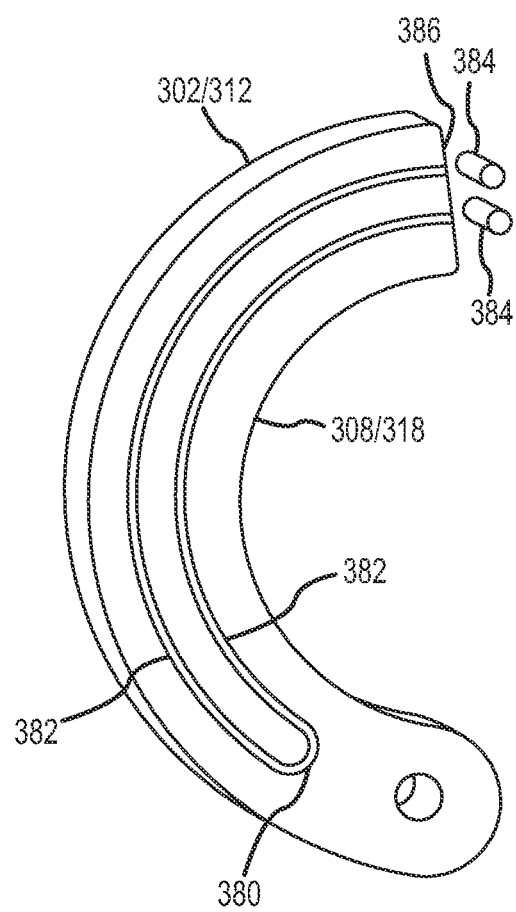
FIG. 10 is a schematic view of another RFID reader antenna layout that may be utilized by the power injector syringe clamp assembly of FIG. 6, along with another option for providing power to an RFID reader antenna.

The first/second clamp member 302/312 shown in FIG. 10 includes an RFID reader antenna section 380, which in turn includes a pair of legs 382 that are spaced from each other. Each leg 382 extends to an edge 386 of the clamp member 302/312, and is aligned with its own electrical contact 384 (e.g., mounted on a powerhead). When the clamp member 302/312 is moved to dispose the clamp assembly 300 into its closed configuration, each leg 382 is brought into electrical contact with its corresponding electrical contact 384. The other clamp member 302/312 could have a similar pair of electrical contacts 384, or the other clamp member 302/312 could also be brought into contact with the electrical contacts 384 shown in FIG. 10.

A power injector syringe clamp assembly of any appropriate size, shape, configuration and/or type (e.g., including any appropriate number of clamp members, including utilizing a single clamp member and where multiple clamp members are utilized and disposed in any appropriate arrangement) may include at least one RFID reader antenna in accordance with the foregoing. In one embodiment, one or more RFID reader antennas are incorporated by a power injector syringe clamp assembly in a manner such that relative positioning requirements between this clamp assembly and an installed power injector syringe are reduced. It may be desirable for each RFID tag on an installed power injector syringe to be readable by one or more RFID reader antennas of the power injector syringe clamp assembly, regardless of its position within the power injector syringe clamp assembly.

One or more clamp members of the power injector syringe clamp assembly may include an RFID reader antenna in accordance with the foregoing. A given RFID antenna may be incorporated with a single clamp member, or may be incorporated with multiple clamp members. Although each clamp member of the power injector syringe clamp assembly could include an RFID reader antenna, it may be such that one or more clamp members will not have any RFID reader antenna included therewith in the case of a multi-clamp member configuration (at least one clamp member, however, will still include at least one RFID reader antenna in such an instance).

The various power injector syringe clamp assemblies described herein may be utilized by any appropriate power injector and may be integrated in any appropriate manner. In one embodiment, the syringe clamp assembly is mounted on a powerhead of the power injector. In another embodiment, the syringe clamp assembly is incorporated into the structure of a faceplate that in turn may be detachably mounted (e.g., by hand or without any tools) to a powerhead of a power injector. In yet another embodiment, the syringe clamp assembly is incorporated into the structure of an adapter that in turn is mounted to a powerhead of a power injector.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed:

1. A power injector syringe clamp assembly, comprising:
   a first clamp member that is movable to at least assist in defining open and closed configurations for said clamp assembly, wherein said first clamp member comprises a first RFID reader antenna on said first clamp member and
   a first pivot pin that is electrically conductive and that is electrically interconnected with said first RFID reader antenna, wherein said first clamp member is mounted on said first pivot pin.

2. The assembly of claim 1, wherein said first clamp member is pivotable between said first and second positions.

3. The assembly of claim 1, further comprising a first electrical contact that is movable, that is biased into engagement with said first pivot pin, and that is electrically interconnected with said first RFID reader antenna.

4. The assembly of claim 1, wherein said first pivot pin comprises a first insulator section and a first pair of conductive sections, wherein said first insulator section is disposed between members of said first pair of conductive sections proceeding along a length dimension of said first pivot pin, wherein said first RFID reader antenna comprises first and second antenna sections that are spaced, wherein said first antenna section is electrically interconnected with one said member of said first pair of conductive sections, and wherein said second antenna section is electrically interconnected with another said member of said first pair of conductive sections.

5. The assembly of claim 1, further comprising a second clamp member.

6. The assembly of claim 5, wherein said second clamp member is maintained in a fixed position.

7. The assembly of claim 5, wherein said second clamp member is movable to at least assist in defining said open and closed configurations for said clamp assembly.

8. The assembly of claim 5, wherein said second clamp member is pivotable.

9. The assembly of claim 5, wherein said second clamp member comprises at least one RFID antenna, wherein said assembly further comprises a second pivot pin that is electrically conductive, and that is electrically interconnected with said at least one RFID reader antenna of said second clamp member, wherein said second clamp member is mounted on said second pivot pin.

10. The assembly of claim 9, further comprising a second electrical contact that is movable, that is biased into engagement with said second pivot pin, and that is electrically interconnected with said at least one RFID reader antenna of said second clamp member.

11. The assembly of claim 9, wherein said second pivot pin comprises a second insulator section and a second pair of conductive sections, wherein said second insulator section is disposed between members of said second pair of conductive sections proceeding along a length dimension of said second pivot pin, wherein said at least one RFID reader antenna of said second clamp member comprises third and fourth antenna sections that are spaced, wherein said third antenna section is electrically interconnected with one said member of said second pair of conductive sections, and wherein said fourth antenna section is electrically interconnected with another said member of said second pair of conductive sections.

12. The assembly of claim 5, wherein said first and second clamp members are each movable about a common axis.

13. The assembly of claim 5, wherein said first and second clamp members are disposed in opposing relation.

14. The assembly of claim 5, wherein one part of said first RFID reader antenna is on said first clamp member and another part of said first RFID reader antenna is on said second clamp member.

15. The assembly of claim 5, further comprising a second RFID reader antenna on said second clamp member.

16. The assembly of claim 15, wherein said first and second RFID reader antennas are disposed on respective surfaces of said first and second clamp members that project toward a barrel of a power injector syringe when positioned within said clamp assembly and with said clamp assembly being in said closed configuration.

17. The assembly of claim 15, wherein said first and second RFID reader antennas are disposed on respective surfaces of said first and second clamp members that project toward a flange of a power injector syringe when positioned within said clamp assembly and with said clamp assembly being in said closed configuration.

18. The assembly of claim 15, wherein said first and second RFID reader antennas are autonomous.

19. The assembly of claim 15, wherein said first and second RFID reader antennas collectively function as a single RFID antenna when said clamp assembly is in said closed configuration.

20. The assembly of claim 1, wherein said first RFID reader antenna is disposed on a surface of said first clamp member that projects toward a barrel of a power injector syringe when s positioned within said clamp assembly and with said clamp assembly being in said closed configuration.

21. The assembly of claim 1, wherein said first RFID reader antenna is disposed on a surface of said first clamp member that projects toward a flange of a power injector syringe when positioned within said clamp assembly and with said clamp assembly being in said closed configuration.

22. The assembly of claim 1, wherein a power injector syringe may be installed in and removed from said power injector syringe clamp assembly when in its said open configuration, and wherein an installed power injector syringe is restrained by said power injector syringe clamp assembly when in its said closed configuration.

23. A power injector, comprising:
a power injector syringe comprising a syringe barrel, a plunger disposed within and movable relative to said syringe barrel, and at least one RFID tag;
a syringe plunger drive assembly that comprises a motorized drive source that interacts with said plunger to move said plunger relative to said syringe barrel; and
a clamp assembly comprising a first clamp member that is movable to at least assist in defining open and closed configurations for said clamp assembly, wherein said first clamp member is disposed in at least one of closely-spaced relation to or in contact with said power injector syringe when said clamp assembly is in said closed configuration, and wherein said first clamp member comprises a first RFID reader antenna.

24. The power injector of claim 23, wherein said at least one RFID tag is on said barrel of said power injector syringe.

25. The power injector of claim 23, wherein said at least one RFID tag is on a flange of said power injector syringe, wherein said flange extends outwardly relative to said syringe barrel on a proximal end of said power injector syringe.

26. The power injector of claim 23, wherein said first clamp member is pivotable between said first and second positions.

27. The power injector of claim 23, wherein said clamp assembly further comprises a first pivot pin that is electrically conductive and that is electrically interconnected with said first RFID reader antenna, wherein said first clamp member is mounted on said first pivot pin.

28. The power injector of claim 23, wherein said clamp assembly further comprises a second clamp member.

29. The power injector of claim 28, wherein said second clamp member is maintained in a fixed position.

30. The power injector of claim 28, wherein said second clamp member is movable to at least assist in defining said open and closed configurations for said clamp assembly.

31. The power injector of claim 28, wherein said second clamp member is pivotable.

32. The power injector of claim 28, wherein said second clamp member comprises at least one RFID antenna, wherein said assembly further comprises a second pivot pin that is electrically conductive, and that is electrically interconnected with said at least one RFID reader antenna of said second clamp member, wherein said second clamp member is mounted on said second pivot pin.

33. The power injector of claim 28, wherein said first and second clamp members are each movable about a common axis.

34. The power injector of claim 28, wherein said first and second clamp members are disposed in opposing relation.

35. The power injector of claim 28, wherein one part of said first RFID reader antenna is on o said first clamp member and another part of said first RFID reader antenna is on said second clamp member.

36. The power injector of claim 28, wherein said clamp assembly further comprises a second RFID reader antenna on said second clamp member.

37. The power injector of claim 36, wherein said first and second RFID reader antennas are disposed on respective surfaces of said first and second clamp members that project toward said syringe barrel of said power injector syringe when positioned within said clamp assembly and with said clamp assembly being in said closed configuration.

38. The power injector of claim 36, wherein said first and second RFID reader antennas are disposed on respective surfaces of said first and second clamp members that project toward a flange of said power injector syringe when positioned within said clamp assembly and with said clamp assembly being in said closed configuration.

39. The power injector of claim 23, wherein said first RFID reader antenna is disposed on a surface of said first clamp member that projects toward said syringe barrel of said power injector syringe when positioned within said clamp assembly and with said clamp assembly being in said closed configuration.

40. The power injector of claim 23, wherein said first RFID reader antenna is disposed on a surface of said first clamp member that projects toward a flange of said power injector syringe when positioned within said clamp assembly and with said clamp assembly being in said closed configuration.

41. The power injector of claim 23, further comprising a flexible connector interconnected with said first RFID reader antenna.

42. The power injector of claim 23, further comprising a first electrical contact that is disposed within a path of motion of said first clamp member, wherein said first electrical contact is spaced from said first RFID reader antenna when said clamp assembly is in said open configuration, and wherein said first electrical contact engages said first RFID reader antenna when said clamp assembly is in said closed configuration.

43. The power injector of claim 23, wherein said power injector syringe may be installed in and removed from said clamp assembly when in its said open configuration, and wherein an installed said power injector syringe is restrained by said clamp assembly when in its said closed configuration.

44. A power injector syringe clamp assembly, comprising:
a first clamp member that is movable to at least assist in defining open and closed configurations for said clamp assembly, wherein said first clamp member comprises a first RFID reader antenna on said first clamp member; and
a flexible connector interconnected with said first RFID reader antenna.

45. A power injector syringe clamp assembly, comprising:
a first clamp member that is movable to at least assist in defining open and closed configurations for said clamp assembly, wherein said first clamp member comprises a first RFID reader antenna on said first clamp member; and
a first electrical contact that is disposed within a path of motion of said first clamp member, wherein said first electrical contact is spaced from said first RFID reader antenna when said first clamp member is in a first position, and wherein said first electrical contact engages said first RFID reader antenna when said first clamp member is in a second position.

* * * * *